(12) United States Patent
Chou

(10) Patent No.: US 8,076,123 B2
(45) Date of Patent: Dec. 13, 2011

(54) EMULSIFICATION-FREE DEGUMMING OF OIL

(75) Inventor: Chih-chung Chou, Yangmei Town (TW)

(73) Assignee: Oilseeds Biorefinery Corporation, George Town, Grand Cayman (KY)

(*) Notice: Subject to any disclaimer, the term of this patent is extended or adjusted under 35 U.S.C. 154(b) by 958 days.

(21) Appl. No.: 11/924,718

(22) Filed: Oct. 26, 2007

(65) Prior Publication Data

US 2009/0111165 A1 Apr. 30, 2009

(51) Int. Cl.
*C11C 1/00* (2006.01)
(52) U.S. Cl. .......... 435/271; 435/41; 435/174; 435/176; 435/177; 435/198; 435/262; 435/267
(58) Field of Classification Search .................... 435/41, 435/174, 176, 177, 198, 262, 267, 271
See application file for complete search history.

(56) References Cited

U.S. PATENT DOCUMENTS

| | | | | |
|---|---|---|---|---|
| 2,683,155 A * | 7/1954 | Dron | ............................. | 554/201 |
| 3,566,871 A * | 3/1971 | Richter et al. | ................ | 604/362 |
| 3,909,381 A * | 9/1975 | Ehrsam | ......................... | 588/302 |
| 4,341,713 A * | 7/1982 | Stolp et al. | ....................... | 554/17 |
| 5,122,365 A * | 6/1992 | Murayama | ....................... | 424/49 |
| 5,265,367 A | 11/1993 | Kinoshita | | |
| 5,558,781 A | 9/1996 | Buchold | | |
| 6,001,640 A | 12/1999 | Loeffler et al. | | |
| 6,162,623 A | 12/2000 | Grote et al. | | |
| 6,407,271 B1 | 6/2002 | Deffense | | |
| 6,426,423 B1 * | 7/2002 | Copeland et al. | ............. | 554/179 |
| 2004/0005604 A1 * | 1/2004 | Gramatikova et al. | ............ | 435/6 |
| 2005/0227945 A1 | 10/2005 | Schmitt et al. | | |
| 2007/0218175 A1 * | 9/2007 | Chou et al. | .................... | 426/417 |

FOREIGN PATENT DOCUMENTS

| | | |
|---|---|---|
| EP | 1 788 080 | 5/2007 |
| JP | 5091889 A * | 4/1993 |
| JP | 06-306386 | 1/1994 |
| JP | 11-228986 | 8/1999 |
| WO | WO 9701632 A1 * | 1/1997 |
| WO | WO 03/102118 | 12/2003 |
| WO | 2006/133698 | 12/2006 |

OTHER PUBLICATIONS

Lee, DH et al. Biodiesel production using a mixture of immobilized Rhizopus oryzae and Candida rugosa lipases. Biotechnology and Bioprocess Engineering. 2006. 11: 522-525.*
Yang et al. "Degumming of Vegetable Oil." Food Technol Biotechnol, 44(1): 101-104. 2006.*
Segers, JC and va de Sande, RLKM. "Degumming—Theory and Practice." Edible Fats and Oils Processing: Basic Principles and Modern Practices. D.R. Erickson (ed.) The American Oil Chemist Society. (place of publication unknown). 1990. pp. 90-93.*
2.P.155, Oil Degumming, in Enzymes in Industry: Production and Applications, edited by Wofgang Aehle, 2nd ed., Wiley-VCH Verlag GmbH & Co. KGaA, 2004.
Yang, J.G., et al, Degumming of Vegetable Oil by a New Microbial Lipase, Food Technol, Biotechnol. 44(1) 101-104(2006).
Use of Lecitase Ultra in degumming vetable oils, Oils & Fats/2002-18255-01.pdg., Novozymes Application Sheet.
Dahike, K., An Enzymatic process for the Physical Refining of Seed Oils,. Chem. Eng. Technol. 21 (1998) pp. 278-281.
Winter, B.H., Komelia Titze and Volker Marschner, Application of phospholipases in the edible oil industry, Fett/Lipid 100 (1998), Nr. 4-5, S. 152-156.
Song 1.K. et al, Phospholipases: Occurrence and production in Microorganisms, Assay for High-Throughput Screening, and Gene Discovery from Natural and Man-Made Diversity, JAOCS vol. 82, No. 10(2005).
Choukri, A. et al., Improved Oil Treatment Conditions for Soft Degumming, JAOCS vol. 78, No. II (2001).
Clausen, K., Enzymatic oil-degumming by a novel microbial phospholipase, Eur. J. Lipid Sci. Technol. 103 (2001) 333-340.
PP. 266-288, Enzymes in Lipid Modification, edited by U.T. Bomscheuer, Wiley-VCH, 2000.
Official Methods and Recommended Practices of the American Oil Chemists' Society, AOCS, Champain (1997) Ca 12-55.

* cited by examiner

*Primary Examiner* — Allison M. Ford
*Assistant Examiner* — Susan E Fernandez
(74) *Attorney, Agent, or Firm* — Thomas, Kayden, Horstemeyer & Risley, LLP

(57) ABSTRACT

This invention relates to an oil degumming method that is free of emulsification. This method includes the steps of treating crude oil first with immobilized phospholipase and then extracting the phospholipase-treated crude oil with pure water or an aqueous solution.

25 Claims, No Drawings

EMULSIFICATION-FREE DEGUMMING OF OIL

BACKGROUND

Crude plant oil, containing phosphatide, cannot be used directly as a biofuel feedstock. More specifically, phosphatide interferes with transesterification, a reaction that a biofuel feedstock is subjected to. Therefore, crude plant oil needs to be refined in a process called oil degumming to remove phosphatide and other undesired substances.

Conventional degumming processes involve emulsification, which poses a number of problems. For example, a high shear mixer, an expensive instrument, is often required to effect emusification. Also, when emulsification is employed, it is often difficult to control degumming quality.

It is therefore desirable to develop a new degumming method that is free of emulsification.

SUMMARY

This invention features an emulsification-free method for removing phosphotide from crude oil. This method includes the following five steps: (1) providing crude oil obtained from a plant or animal source containing nonhydratable phosphatide, (2) treating the crude oil with immobilized phospholipase to effect conversion of the nonhydratable phosphatide to hydratable phosphatide, (3) mixing the treated crude oil with pure water or an aqueous solution to form a mixture having an oil phase and a water phase, (4) allowing separation of the oil phase and the water phase, and (5) collecting the oil phase.

The crude oil used in step (1) can be extracted from a plant (e.g., soybean or sunflower) with a suitable solvent (e.g., fatty acid alkyl ester or hexane). The crude oil can also be obtained by separating fat from an animal source and then mixing the fat with a suitable solvent (e.g., fatty acid alkyl ester). When fatty acid alkyl ester is used, it is preferably obtained by reacting alcohol with triglyceride extracted from the same plant or animal source.

The phospholipase used in step (2) can be PLA1, PLA2, PLC, PLD, or a combination thereof. This step is free of emulsification.

In step (3), the treated crude oil can be mixed with an aqueous solution containing an acid (e.g., citric acid, lactic acid, fumaric acid, tartaric acid, or phosphoric acid), a chelating agent (e.g., ethylenediaminetetraacetic acid, β-alaninediacetic acid, nitrilotriacetic acid, diethylene triamine pentaacetic acid, hydroxyethylethylenediaminetriacetic acid, or iminodiacetate), or both. The aqueous solution can further contain a surfactant, e.g., sodium dodecyl sulfate or lauryl sulphate. Step (3) is also free of emulsification.

The method of this invention can include an additional step. Namely, the crude oil, before treated with phospholipase, is extracted with pure water or the aqueous solution described above to remove water-soluble substances.

The details of one or more implementations of the invention are set forth in the description below. Other features, objects, and advantages of the invention will be apparent from the description and from the claims.

DETAILED DESCRIPTION

The present invention aims at degumming oil, i.e., removing phosphatide and other undesired substances from crude oil. The oil degumming is achieved by first treating crude oil, free of emulsification, with phospholipase and then extracting the phospholipase-treated crude oil with water/aqueous solution, also free of emulsification.

More specifically, crude oil, obtained from either a plant or animal source (e.g., a livestock), is treated by immobilized phospholipase. Exemplary plants include but are not limited to soybean, peanut, sunflower seed, rapeseed, corn, jatropha seed, karanja seed, neem seed, mahua seed, castor bean, rubber seed, cotton seed, palm kernel, olive, almond kernel, babassu seed, ben seed, cardoon seed, camelina seed, linseed, hazelnut kernel, hemp seed, mustard seed, jojoba seed, poppy seed, safflower seed, sesame seed, wheat grain, sal seed, crambe seed, cuphea seed, nahor seed, tobacco seed, alage, rice bran, palm fruit pulp, yellowwood, or others described in US Patent Application 20070218175.

The crude oil can be prepared by methods well known in the art, e.g., extracting a plant with a suitable solvent or rendering an animal tissue. The term "rendering" refers to a process that separates fat from animal tissue, e.g., fatty tissue, bone, and offal. In one example, the crude oil is prepared by extracting a plant with fatty acid alkyl ester obtained by reacting alcohol with triglyceride extracted from the same plant. See US Patent Applications 2006/0063241 and 2007/0218175. In another example, the crude oil is obtained by rendering animal fatty tissue to produce fat and then mixing the fat with fatty acid alkyl ester. The crude oil is then treated with immobilized phospholipase. To obtain immobilized phospholipase, one or more types of phospholipase are attached onto a suitable carrier by adsorption or other methods well known in the art. See Enzymes in Lipid Modification, edited by U. T. Bornscheuer, Wiley-VCH, pages 266-288 (2000). A suitable carrier is one that does not inhibit activity of the enzyme immobilized on it. The carrier, with the phospholipase attached, is placed in a reactor, e.g., a fixed bed reactor or a continuous stirred-tank reactor. The reactor can be filled with the crude oil either before or after the carrier is placed in it. The immobilized phospholipase converts nonhydratable phosphatide in the crude oil to hydratable phosphatide. The term "phosphatide" used herein covers various types of phosphatides derived from any plant or animal source. This enzymatic reaction, free of emulsification, is performed at a suitable temperature (i.e., 10 to 100° C., preferably 10 to 75° C., or 10 to 50° C.) for an adequate time to allow maximal conversion.

The phospholipase-treated crude oil is then subjected to extraction with pure water or an aqueous solution containing a chelating agent or an acid to remove the resultant hydratable phosphatide and other undesired substances. This extracting process is also free of emulsification. An example follows. The phospholipase-treated crude oil is transferred from the reactor to another container, and mixed therein with water at a water to oil ratio (v:v) of 0.05:1-2.0:1, preferably 0.1:1-1.5:1. The mixture thus formed is agitated for an adequate time at a suitable temperature. After agitation, the mixture is allowed to sit still until an oil phase and a water phase form. Alternatively, the mixture is centrifuged to achieve water-oil separation. The oil phase is then collected. The above-described enzymatic reaction and extracting process can be performed sequentially for one or more times.

It is preferred that, before treated with phospholipase, the crude oil be extracted with pure water or an aqueous solution following the same procedures described above. In one example, the crude oil is extracted with an aqueous solution containing 1% EDTA (w/v) as follows. The crude oil is mixed with the EDTA solution in a container. The mixture thus formed is agitated for an adequate time at a suitable temperature and then allowed to separate into a water phase and an oil phase. The oil phase is then treated by the immobilized phospholipase as described above.

The degummed oil, obtained from the method of this invention, can be used as a feedstock of biofuel. It also can be used in food or oleochemical industry.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Emulsification-Free Degumming of Crude Oil

Crude oil was extracted from soybean powder with hexane. The crude oil, obtained after removal of hexane by evaporation, was mixed with fatty acid methyl ester to prepare two oil solutions, one containing 33.3% by weight oil (33.3% oil solution), and the other containing 10.0% by weight oil (10% oil solution).

Lecitase Ultra (PLA1; obtained from Novozymes, Denmark) was immobilized on methacrylate particles (porous crosslinked) having a size of 0.3-1.0 mm by physical adsorption. 0.65 g immobilized PLA1 was incubated in fatty acid methyl ester overnight and then transferred to three 100 ml flasks, each containing 5.7 g of 100% crude oil, 33.3% oil solution and 10.0% oil solution, respectively. The flasks were shaken for 60 minutes at 200 rpm to facilitate contact of the oil/oil solution to PLA1. The enzymatic reaction was conducted at 25° C. and the immobilized PLA1 was then removed upon completion of the reaction.

An aqueous solution containing 1% EDTA (w/v) was mixed with the PLA1-treated oil or oil solution at a ratio of 1:1 (v/v). The mixture thus formed was shaken at 25° C., 200 rpm for 60 minutes and then centrifuged at 6,000 rpm for 15 minutes to effect formation of an oil phase from an aqueous phase. The oil phase was collected for phosphorus analysis, following the American Oil Chemists Society method Ca 12-55 (14).

In another implementation, before the PLA1 treatment, the crude oil was pre-treated with water to remove water-soluble substances contained therein. Briefly, the crude oil was mixed with water at a ratio of 1:1 (v/v) and heated to 75-80° C. for 15 minutes. After cooling to room temperature, the oil-water mixture was centrifuged at 6,000 rpm for 15 minutes to allow formation of an oil phase and a water phase. The oil phase was collected and subjected to the PLA1/EDTA treatment as described above.

Table 1 below shows that PLA1/EDTA treatment significantly lowered the concentrations of phosphorus (corresponding to phosphatide levels) in the crude oil and oil solutions, and that water pretreatment further lowered the concentrations of phosphorus in these oil samples.

TABLE 1

Phosphorus Concentrations in Oil Samples Before and After PLA1/EDTA Treatment

| Oil Sample | Crude Oil | 33.3% Oil Solution | 10% Oil Solution |
|---|---|---|---|
| Concentration of Phosphorus before PLA1/EDTA treatment (ppm) | 252.62 | 85.16 | 24.31 |
| Concentration of Phosphorus after PLA1/EDTA treatment (ppm) | 12.16 | 18.18 | 7.44 |

TABLE 1-continued

Phosphorus Concentrations in Oil Samples Before and After PLA1/EDTA Treatment

| Oil Sample | Crude Oil | 33.3% Oil Solution | 10% Oil Solution |
|---|---|---|---|
| Concentration of Phosphorus after water pre-treatment and PLA1/EDTA treatments (ppm) | 8.12 | 11.17 | 9.69 |

The effect of fatty acid methyl ester on degumming efficiency was also studied. The crude oil was first pretreated by water and then mixed with fatty acid methyl ester to obtain solutions containing 75%, 66.66%, 50%, and 33.33% by weight oil. The oil solutions were subjected to the PLA1/EDTA treatment as described above. Results thus obtained indicate that fatty acid methyl ester did not affect the efficiency of this degumming process. More specifically, after the PLA1/EDTA treatment, the phosphorus levels in the crude oil (pretreated with water) and in the 75%, 66.66%, 50%, and 33.33% oil solutions decreased from 44.95 ppm to 2.94 ppm, from 39.77 ppm to 5.54 ppm, from 33.47 ppm to 3.71 ppm, from 24.75 ppm to 3.56 ppm, and from 17.0 ppm to 6.56 ppm, respectively. These results further indicate that PLA1/EDTA treatment decreased phosphorus levels in the crude oil and the oil solutions, all of which contained different concentrations of non-hydratable phosphatide, to a similar level. In other words, the concentrations of non-hydratable phosphatide also did not affect the degumming efficiency.

Finally, it was studied whether the temperature of PLA1 treatment would affect the degumming efficiency. The crude oil pre-treated with water, containing 44.95 ppm phosphorus, was subjected to PLA1 treatment at 25, 35, 40, 50, or 60° C. Each of the treated oil samples was then extracted with 1% EDTA and its phosphorus level was determined. Results indicate that the tested temperatures did not affect the degumming efficiency. More specifically, similar phosphorus levels (ranging from 3.19 ppm to 8.27 ppm) were detected in the crude oil samples treated with PLA1 at the various temperatures mentioned above followed by EDTA extraction.

Example 2

Extracting Lipase-Treated Oil With Aqueous Solutions Containing Different Chelating Agents or Acids The crude oil as described in Example 1 was pre-treated by water and then subjected to Lecitase Ultra (PLA1) treatment following the methods described above. The PLA1-treated crude oil was mixed with an aqueous solution containing 1% (w/v) ethylenediaminetetraacetic acid (EDTA), β-alaninediacetic acid (ADA), nitrilotriacetic acid (NTA) or diethylene triamine pentaacetic acid (DTPA) at a ratio of 1:1 (v/v). The mixture thus produced was shaken at 25° C., 200 rpm for 60 minutes, and then centrifuged at 6,000 rpm for 15 minutes to form an oil phase and a water phase. The oil phase was collected for phosphorus analysis.

As shown in Table 2, aqueous solutions containing EDTA, DTPA, NTA, and ADA were all effective in removing hydratable phosphatide from the PLA1-treated crude oil. Among them, aqueous solutions containing EDTA and DTPA were most effective.

In another implementation, the PLA1-treated crude oil was extracted with pure water or an aqueous solution containing lactic acid, citric acid, or fumaric acid. Also shown in Table 2, these aqueous solutions were all effective in removing hydratable phosphatide from the PLA1-treated crude oil.

TABLE 2

Phosphorus Concentrations in Crude Oil Samples Treated with Lipase and Extracted with Aqueous Solutions Containing Different Chelating Agents or Acids

| Aqueous Solutions | EDTA | NTA | DTPA | ADA | Water | Lactic Acid | Citric Acid | Fumaric Acid |
|---|---|---|---|---|---|---|---|---|
| Phosphorus Con. before treatment (ppm) | 44.95 | 44.95 | 44.95 | 44.95 | 44.95 | 44.95 | 44.95 | 44.95 |
| Phosphorus Cons. after treatment (ppm) | 4.68 | 8.78 | 4.81 | 11.43 | 13.55 | 13.63 | 11.17 | 10.63 |

Example 3

Treating Crude Oil with Different Types of Phospholipase

Different phospholipases, shown in Table 3, were used to treat the crude oil or the 33.3% oil solution (described in Example 1), following the procedures also described in Example 1.

TABLE 3

Phosphorus Concentrations in oil samples treated with different phospholipases

| Lipase | Source | Type | P Con. in Crude Oil (ppm) Before | P Con. in Crude Oil (ppm) After | P Con. in 33% Oil Solution (ppm) Before | P Con. in 33% Oil Solution (ppm) After |
|---|---|---|---|---|---|---|
| Lecitase Ultra | Novozymes, Denmark | $PLA_1$ | 42.85 | 5.01 | 17.51 | 5.01 |
| PLC | Asahi Kasei, Japan | PLC | | 8.86 | | 5.5 |
| $PLA_2L$ | Asahi Kasei, Japan | $PLA_2$ | | 17.75 | | 4.59 |
| PLD | Asahi Kasei, Japan | PLD | | 8.06 | | N.A. |
| PLDP | Asahi Kasei, Japan | PLD | | 3.02 | | N.A. |

As shown in Table 3, PLA1, PLA2, and PLC exhibited equal effectiveness in reducing phosphorus concentrations in the 33.3% oil solution, and that PLA1, PLC, and PLD were effective in reducing phosphorus concentrations in the crude oil. These results indicate that various phospholipases can be used in the oil-degumming method of this invention.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for removing phosphatide from crude oil obtained from a plant or animal source, the method comprising:
   providing crude oil containing nonhydratable phosphatide,
   treating the crude oil with immobilized phospholipase, free of emulsification, to effect conversion of the nonhydratable phosphatide to hydratable phosphatide,
   mixing the treated crude oil with pure water or an aqueous solution, free of emulsification, to form a mixture having an oil phase and an aqueous phase,
   allowing separation of the oil phase and the aqueous phase, and
   collecting the oil phase.

2. The method of claim 1, wherein the plant is soybean, peanut, sunflower seed, rapeseed, corn, jatropha seed, karanja seed, neem seed, mahua seed, castor bean, rubber seed, cotton seed, palm kernel, olive, almond kernel, babassu seed, ben seed, cardoon seed, camelina seed, linseed, hazelnut kernel, hemp seed, mustard seed, jojoba seed, poppy seed, safflower seed, sesame seed, wheat grain, sal seed, crambe seed, cuphea seed, nahor seed, tobacco seed, alage, rice bran, palm fruit pulp, or yellowwood.

3. The method of claim 1, wherein the crude oil is obtained by extracting the plant with fatty acid alkyl ester and contains the fatty acid alkyl ester.

4. The method of claim 3, wherein the fatty acid alkyl ester is obtained by reacting alcohol with triglyceride extracted from the same plant.

5. The method of claim 3, wherein the phospholipase is PLA1, PLA2, PLC, PLD, or a combination thereof.

6. The method of claim 3, wherein the mixing step is performed by mixing the treated crude oil with an aqueous solution, the aqueous solution containing a chelating agent, an acid, or both.

7. The method of claim 6, wherein the chelating agent is selected from the group consisting of ethylenediaminetetraacetic acid, β-alaninediacetic acid, nitrilotriacetic acid, diethylene triamine pentaacetic acid, hydroxyethylethylenediaminetriacetic acid, and iminodiacetate.

8. The method of claim 6, wherein the acid is selected from the group consisting of citric acid, lactic acid, fumaric acid, tartaric acid, and phosphoric acid.

9. The method of claim 1, wherein the crude oil is obtained by separating fat from the animal source and mixing the fat with fatty acid alkyl ester.

10. The method of claim 9, wherein the fatty acid alkyl ester is obtained by reacting alcohol with triglyceride extracted from the same animal source.

11. The method of claim 9, wherein the phospholipase is $PLA_1$, $PLA_2$, PLC, PLD or a combination thereof.

12. The method of claim 9, wherein the mixing step is performed by mixing the treated crude oil with an aqueous solution, the aqueous solution containing a chelating agent, an acid, or both.

13. The method of claim 12, wherein the chelating agent is selected from the group consisting of ethylenediaminetetraacetic acid, β-alaninediacetic acid, nitrilotriacetic acid, diethylene triamine pentaacetic acid, hydroxyethylethylenediaminetriacetic acid, and iminodiacetate.

14. The method of claim 12, wherein the acid is selected from the group consisting of citric acid, lactic acid, fumaric acid, tartaric acid, and phosphoric acid.

15. The method of claim 1, wherein, before the treating step, the crude oil is extracted with pure water or an aqueous solution to remove water-soluble substances contained therein.

16. The method of claim 15, wherein the aqueous solution contains a chelating agent, an acid, or both.

17. The method of claim 16, wherein the chelating agent is selected from the group consisting of ethylenediaminetetraacetic acid, β-alaninediacetic acid, nitrilotriacetic acid, and diethylene triamine pentaacetic acid, hydroxyethylethylenediaminetriacetic acid, and iminodiacetate.

18. The method of claim 16, wherein the acid is selected from the group consisting of citric acid, lactic acid, fumaric acid, tartaric acid, and phosphoric acid.

19. The method of claim 1, wherein the phospholipase is PLA1, PLA2, PLC, PLD or a combination thereof.

20. The method of claim 1, wherein the treating step is performed at a temperature between 10° C. to 75° C.

21. The method of claim 1, wherein the mixing step is performed by mixing the treated crude oil with an aqueous solution, the aqueous solution containing a chelating agent, an acid, or both.

22. The method of claim 21, wherein the chelating agent is selected from the group consisting of ethylenediaminetetraacetic acid, β-alaninediacetic acid, nitrilotriacetic acid, diethylene triamine pentaacetic acid, hydroxyethylethylenediaminetriacetic acid, and iminodiacetate.

23. The method of claim 21, wherein the acid is selected from the group consisting of citric acid, lactic acid, fumaric acid, tartaric acid, and phosphoric acid.

24. The method of claim 21, wherein the aqueous solution further contains a surfactant.

25. The method of claim 24, wherein the surfactant is sodium dodecyl sulfate or lauryl sulphate.

* * * * *